United States Patent [19]
Duchon et al.

[11] Patent Number: 5,964,718
[45] Date of Patent: Oct. 12, 1999

[54] BODY FLUID SAMPLING DEVICE

[75] Inventors: Brent G. Duchon, San Jose; Jeffrey N. Roe, San Ramon; Ryszard Radwanski, Morgan Hill; Joel S. Douglas, Santa Clara, all of Calif.

[73] Assignee: Mercury Diagnostics, Inc., Scotts Valley, Calif.

[21] Appl. No.: 08/975,978

[22] Filed: Nov. 21, 1997

[51] Int. Cl.⁶ .................................................... A61B 5/00
[52] U.S. Cl. .......................................... 600/583; 606/181
[58] Field of Search .................................... 600/573, 576, 600/583; 606/181–183

[56] References Cited

U.S. PATENT DOCUMENTS

| | | |
|---|---|---|
| D. 254,444 | 3/1980 | Levine . |
| 4,360,016 | 11/1982 | Sarrine . |
| 4,503,856 | 3/1985 | Cornell et al. . |
| 4,517,978 | 5/1985 | Levin et al. . |
| 4,622,974 | 11/1986 | Coleman et al. . |
| 4,627,445 | 12/1986 | Garcia et al. . |
| 4,637,403 | 1/1987 | Garcia et al. . |
| 4,648,408 | 3/1987 | Hutcheson et al. . |
| 4,653,511 | 3/1987 | Goch . |
| 4,653,513 | 3/1987 | Dombrowski . |
| 4,658,821 | 4/1987 | Chiodo et al. . |
| 4,685,463 | 8/1987 | Williams . |
| 4,687,000 | 8/1987 | Eisenhardt et al. . |
| 4,787,398 | 11/1988 | Garcia et al. . |
| 4,790,979 | 12/1988 | Terminiello et al. . |
| 4,805,623 | 2/1989 | Jobsis . |
| 4,850,973 | 7/1989 | Jordan et al. . |
| 4,858,607 | 8/1989 | Jordan et al. . |
| 4,873,993 | 10/1989 | Meserol et al. . |
| 4,883,068 | 11/1989 | Dechow . |

(List continued on next page.)

FOREIGN PATENT DOCUMENTS

| | | |
|---|---|---|
| 0453283 | 10/1991 | European Pat. Off. . |
| 0 671 146 | 9/1995 | European Pat. Off. . |
| 0 688 532 | 12/1995 | European Pat. Off. . |
| 3708031 | 11/1987 | Germany . |
| WO 8504089 | 9/1985 | WIPO . |
| WO 9510223 | 4/1995 | WIPO . |
| WO 97 42885 | 11/1997 | WIPO . |
| WO 97 43962 | 11/1997 | WIPO . |
| WO 9743962 | 11/1997 | WIPO . |

OTHER PUBLICATIONS

Ash, et al., "A Subcutaneous Capillary Filtrate . . . ," ASAIO Journal, 1993, pp. M699–M705.
Ash, et al., "Subcutaneous Capillary Filtrate . . . " ASAIO Journal, 1992, pp. M416–M420.
Critical Reviews in Biochemical Engineering, vol. 18, issue 1, 1990, pp. 29–54.
Brace, et al., "Reevaluation of the needle . . . ," Amer Jrnal of Phy, v 229, 1975, pp. 603–607.
Ginsberg., "An Overview of Minimally . . . ," Clinical Chem, v 38, 1992, pp. 1596–1600.
Janle–Swain, et al., "Use of Capillary . . . ," Trans Am Soc Artif Intern Organs, 1987, p 336–40.
Kayashima, et al., "Suction effusion fluid from . . . ," Amer Phys Soc, 1992, pp H1623–1626.
Korthuis, et al., "Interstitium & Lymphatic Techniques," pp. 326–327.
Turner, et al., "Diabetes Mellitus: Biosensors for . . . ," Bioscensors, 1985, pp. 85–115.
"Microlet Choice" Low Pressure Blood Sampling Instrument Ad with translation, Jun. 1997.

*Primary Examiner*—Max Hindenburg
*Attorney, Agent, or Firm*—Burns, Doane, Swecker & Mathis, L.L.P.

[57] ABSTRACT

Body fluid is sampled from a skin incision by placing a ring against the skin and repeatedly applying an elastic pressing force to the ring, whereby a stimulator surface of the ring depresses a ring of skin and body tissue in surrounding relationship to the incision to force body fluid from the incision. The stimulator surface is inclined at an angle of 10 to 65 degrees; a width of the stimulator surface is from 5 mm to 20 mm, and an inner diameter of the stimulator surface is no less than 6.0 mm.

23 Claims, 10 Drawing Sheets

U.S. PATENT DOCUMENTS

| | | |
|---|---|---|
| 4,920,977 | 5/1990 | Haynes . |
| 4,924,879 | 5/1990 | O'Brien . |
| 4,953,552 | 9/1990 | DeMarzo . |
| 4,976,724 | 12/1990 | Nieto et al. . |
| 4,994,068 | 2/1991 | Hufnagle . |
| 4,994,073 | 2/1991 | Green . |
| 5,002,054 | 3/1991 | Ash et al. . |
| 5,014,718 | 5/1991 | Mitchen . |
| 5,029,583 | 7/1991 | Meserol et al. . |
| 5,054,499 | 10/1991 | Swierczek . |
| 5,066,859 | 11/1991 | Karkar et al. . |
| 5,070,886 | 12/1991 | Mitchen et al. . |
| 5,163,442 | 11/1992 | Ono . |
| 5,165,418 | 11/1992 | Tankovich . |
| 5,201,324 | 4/1993 | Swierczek . |
| 5,217,480 | 6/1993 | Haber et al. . |
| 5,231,993 | 8/1993 | Haber et al. . |
| 5,277,198 | 1/1994 | Kanner et al. . |
| 5,318,584 | 6/1994 | Lange et al. . |
| 5,320,607 | 6/1994 | Ishibashi . |
| 5,368,047 | 11/1994 | Suzuki et al. . |
| 5,395,387 | 3/1995 | Burns . |
| 5,402,798 | 4/1995 | Swierczek et al. . |
| 5,569,212 | 10/1996 | Brown . |
| 5,582,184 | 12/1996 | Erickson et al. . |
| 5,628,309 | 5/1997 | Brown . |
| 5,628,764 | 5/1997 | Schraga . |

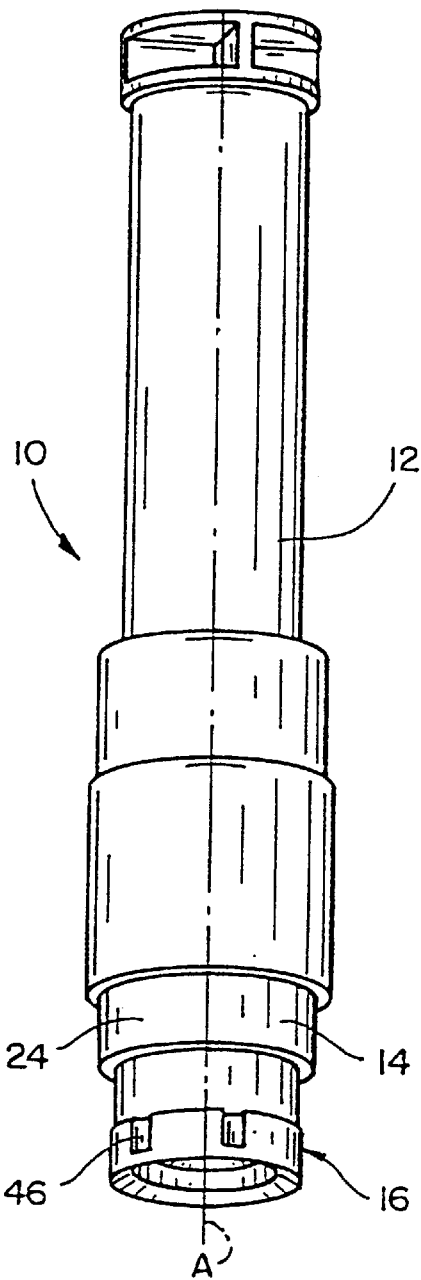
FIG_1
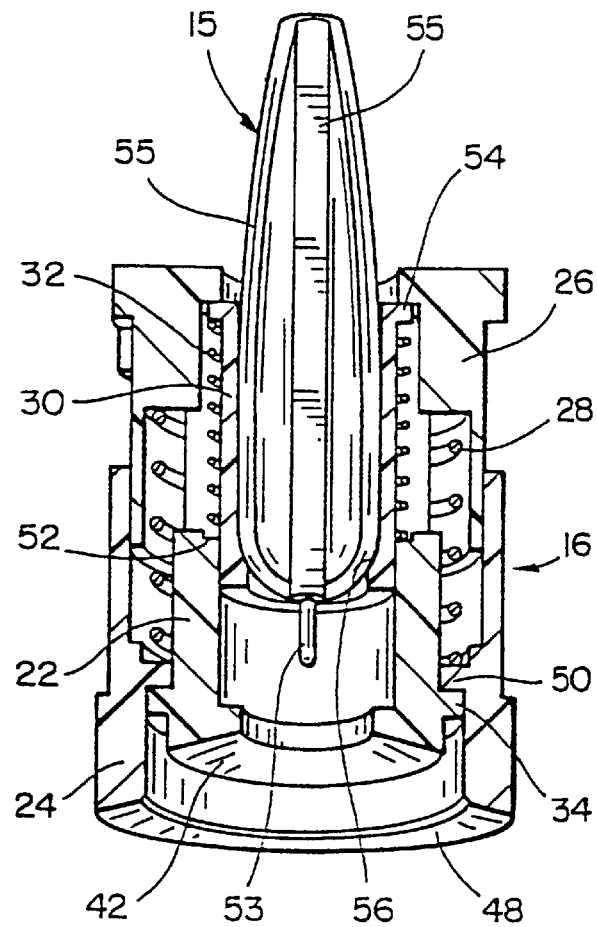
FIG_2

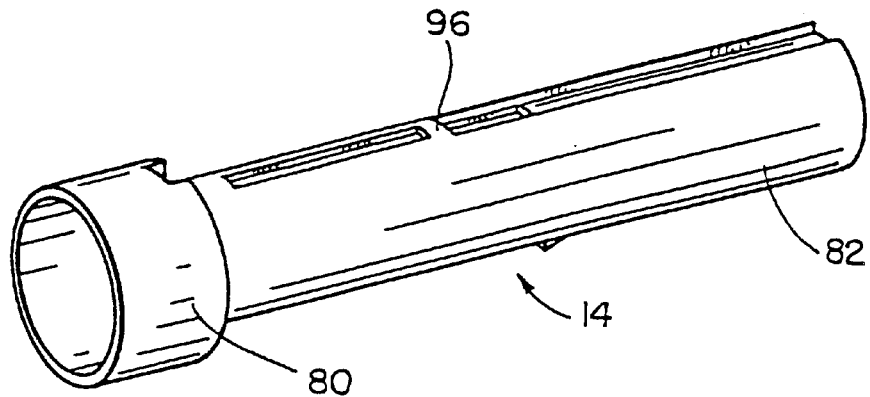
FIG_3
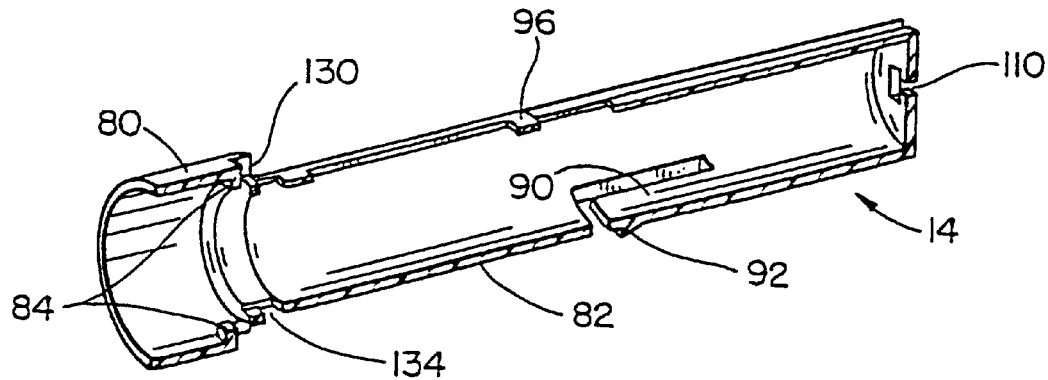
FIG_4
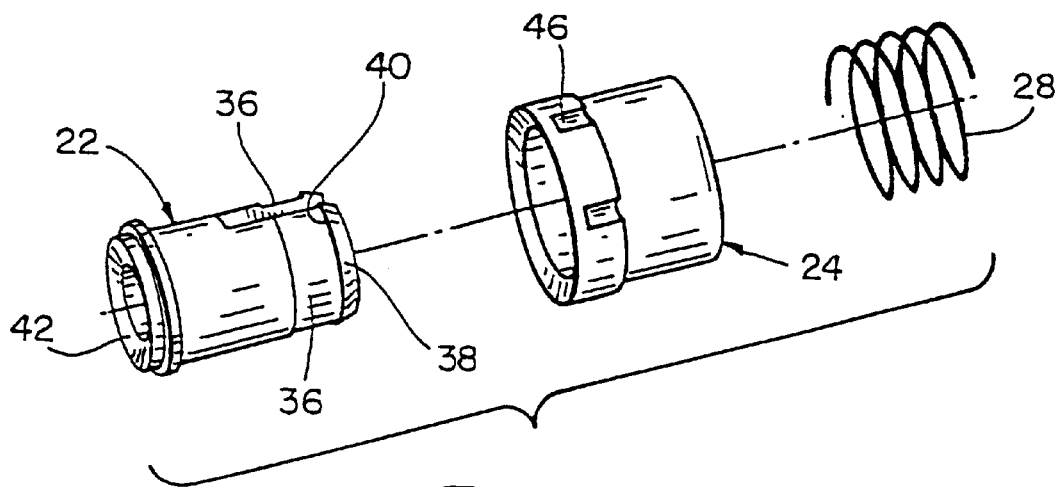
FIG_5

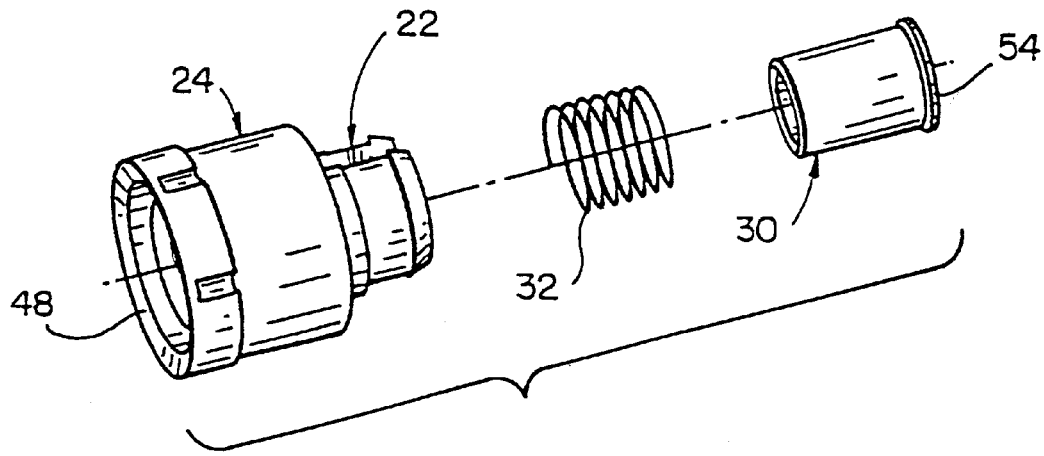
FIG_6
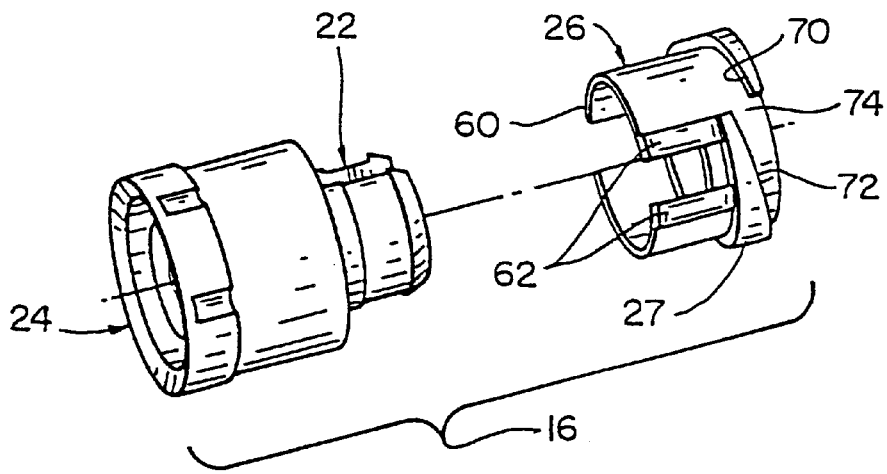
FIG_7
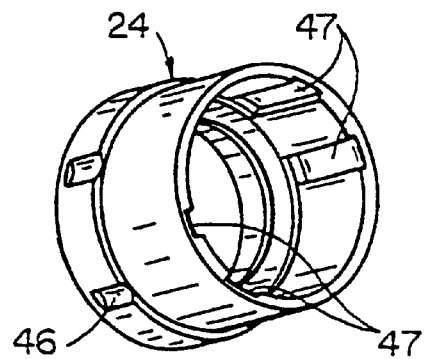
FIG_8

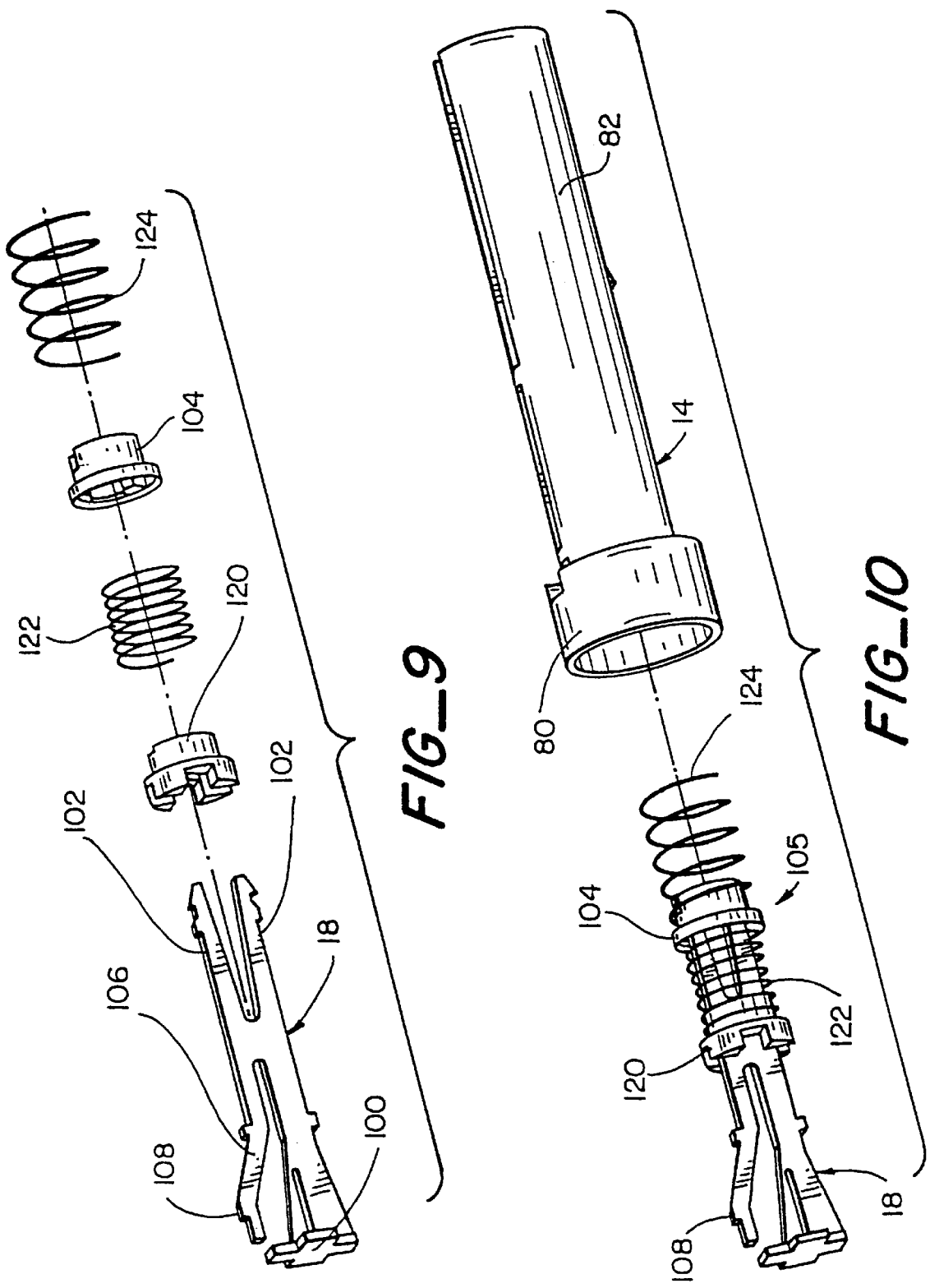

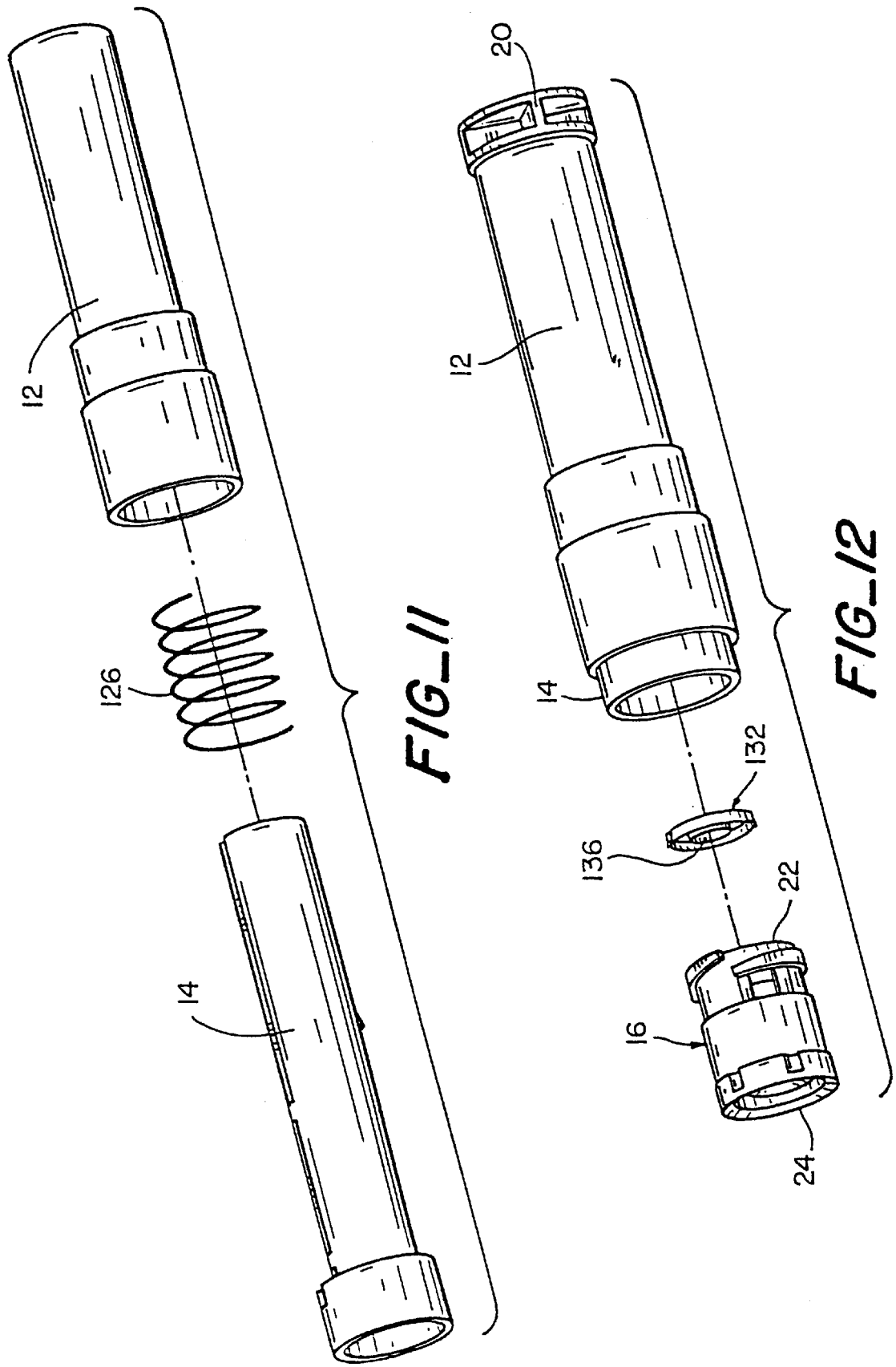

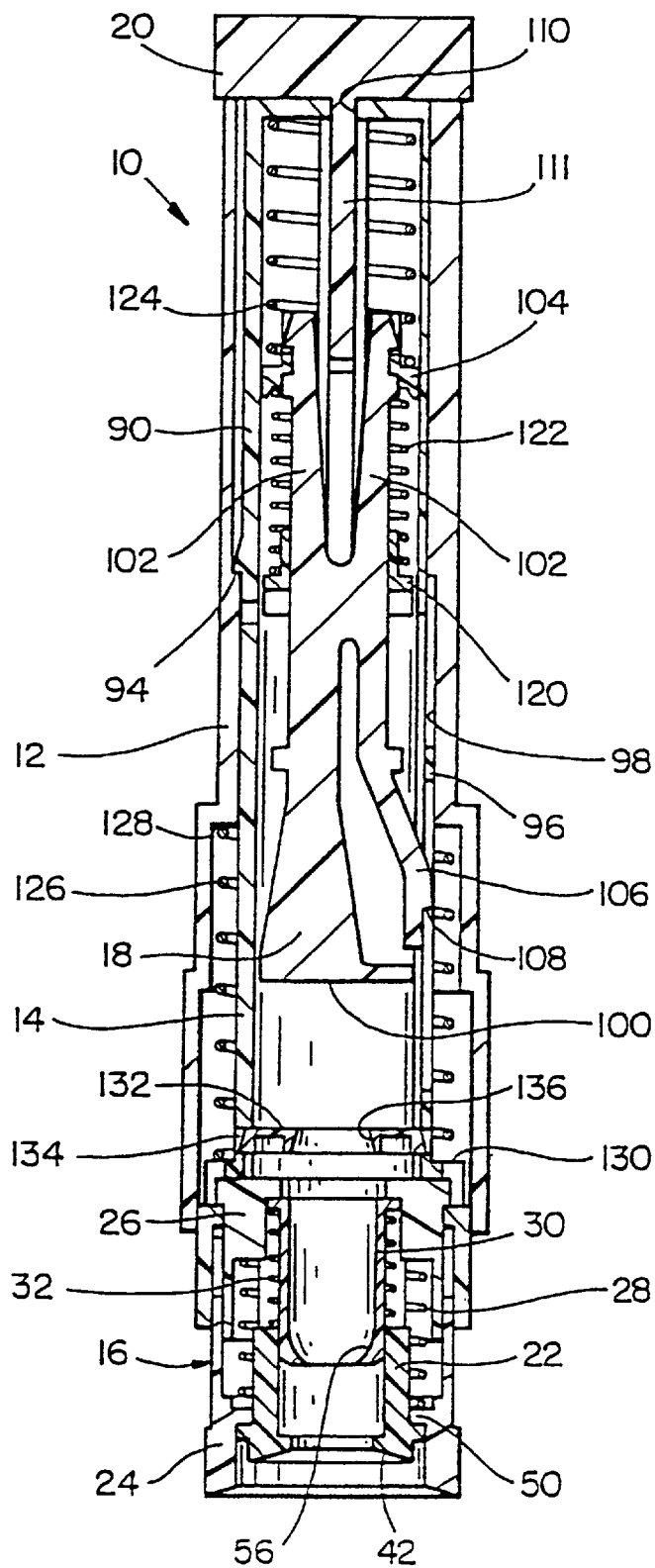
FIG_13A

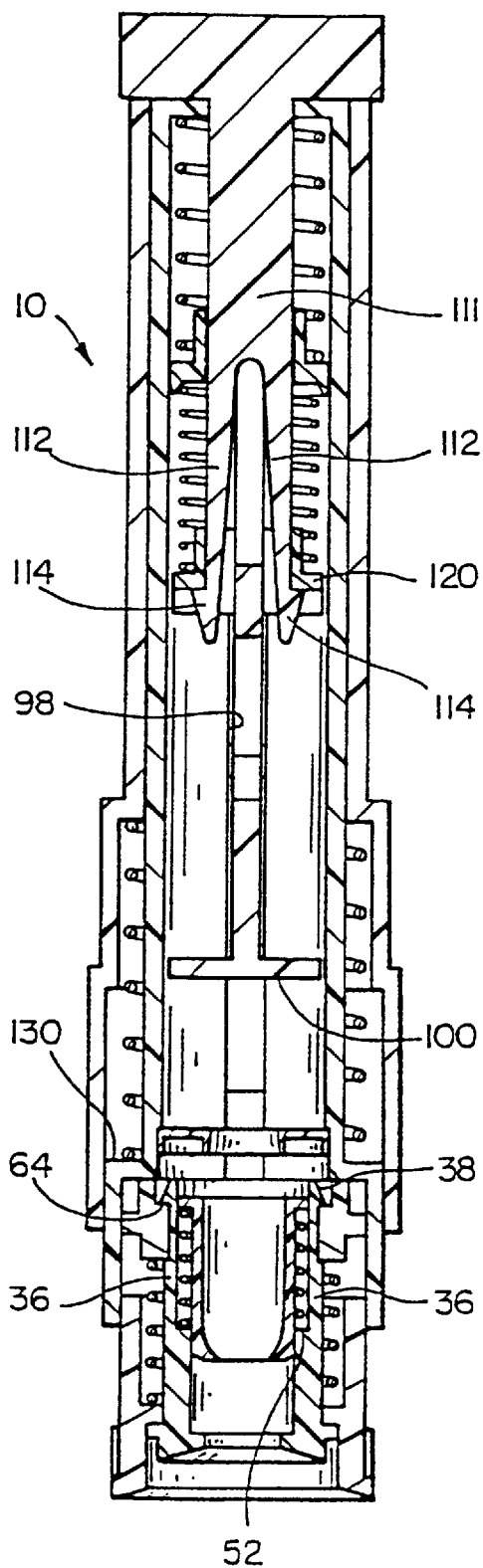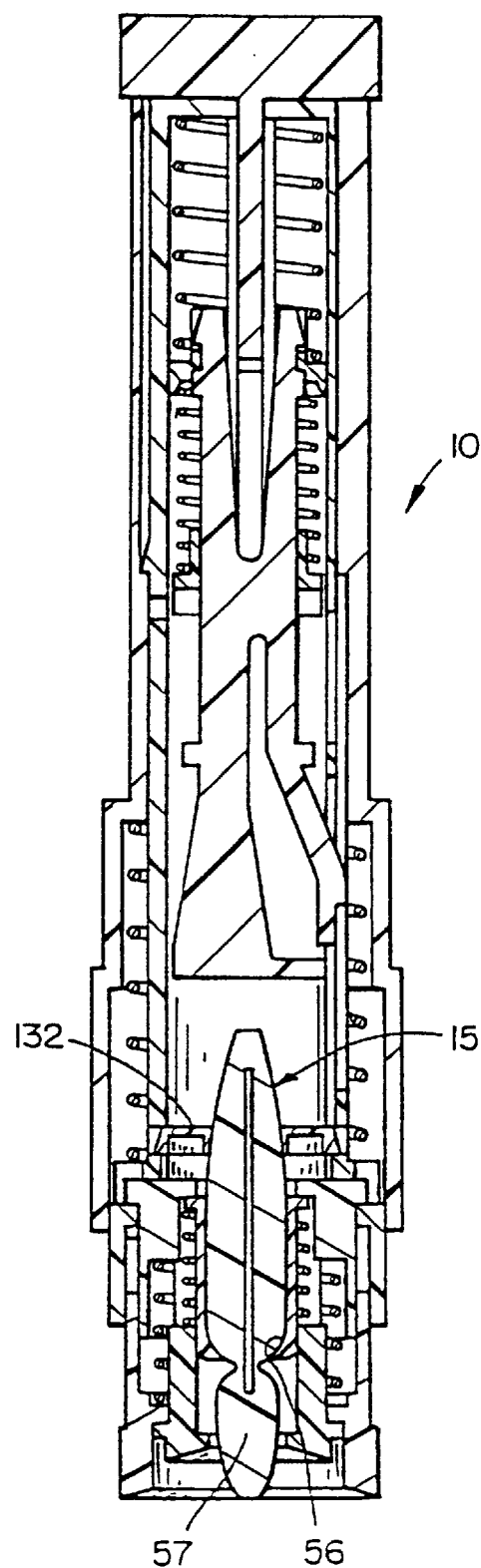
FIG_13B  FIG_13C

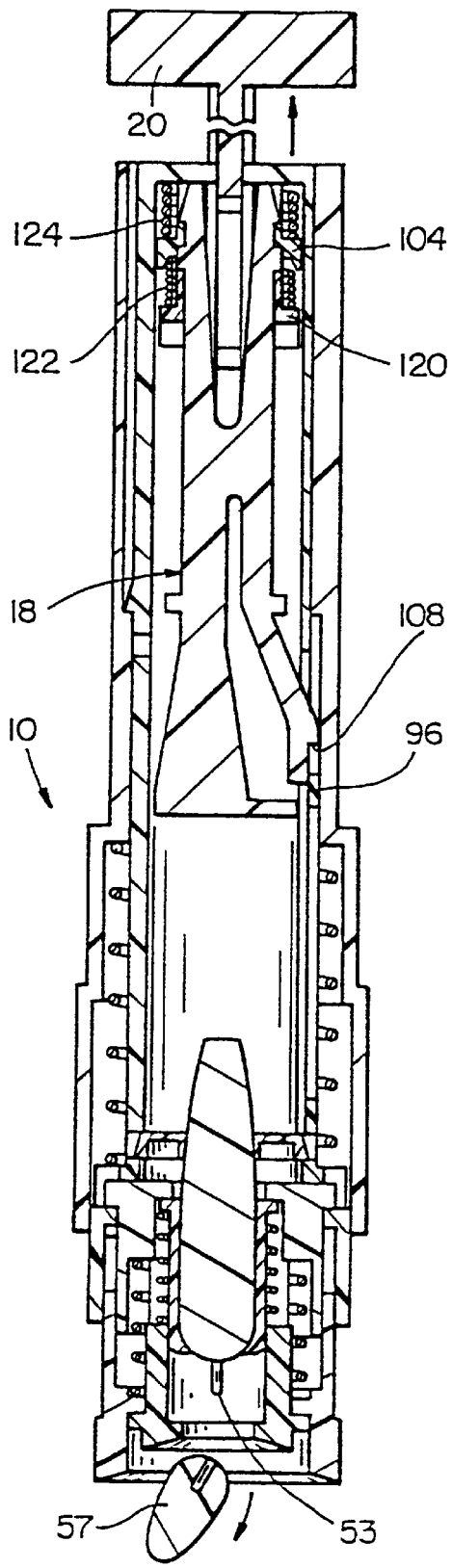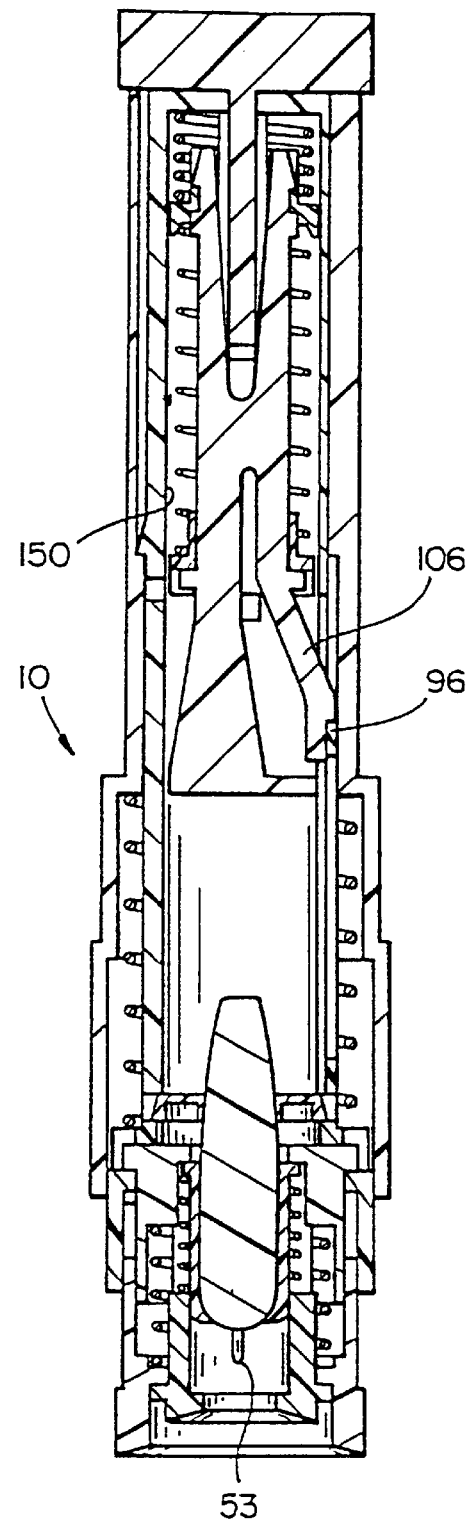
FIG_13D  FIG_13E

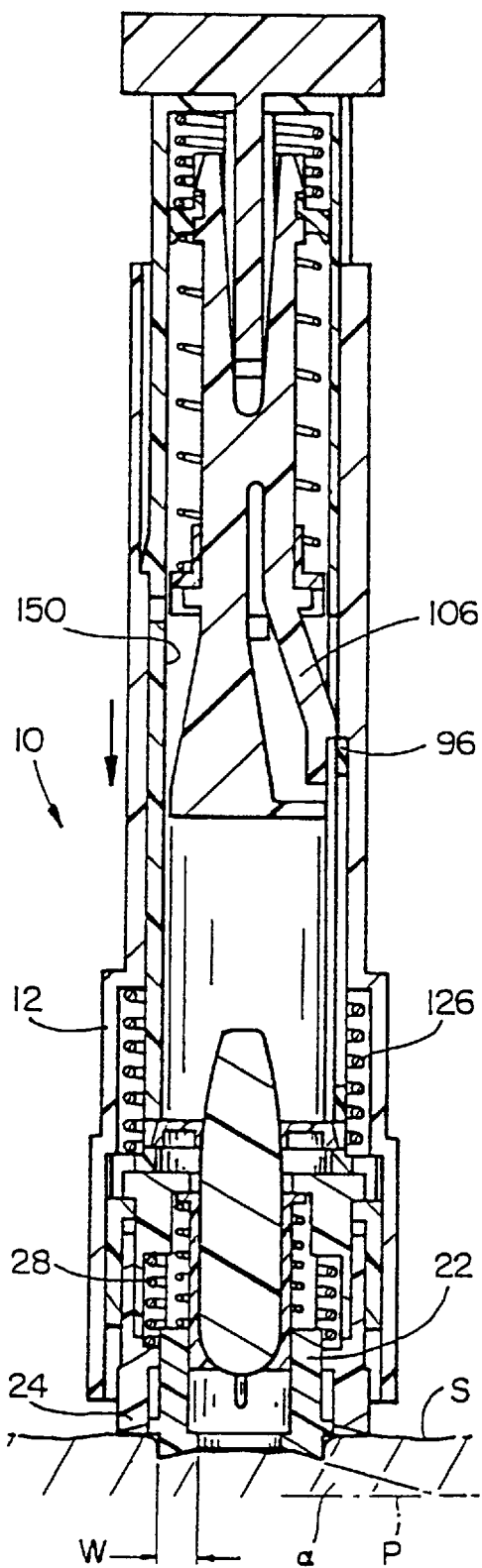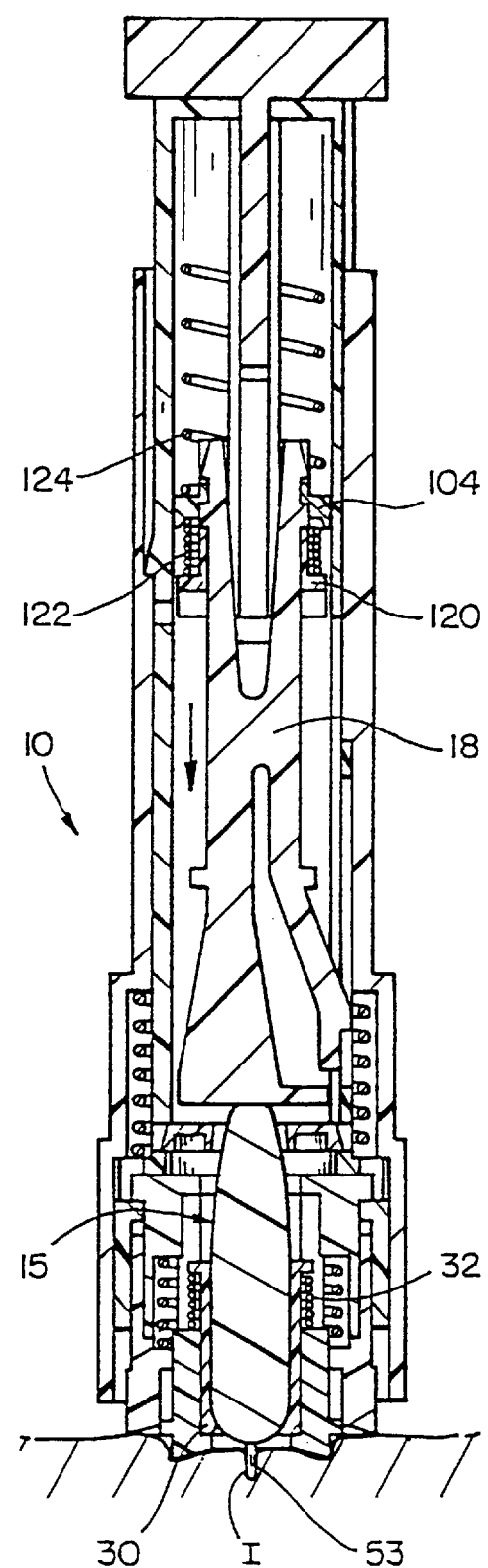
FIG_13F  FIG_13G

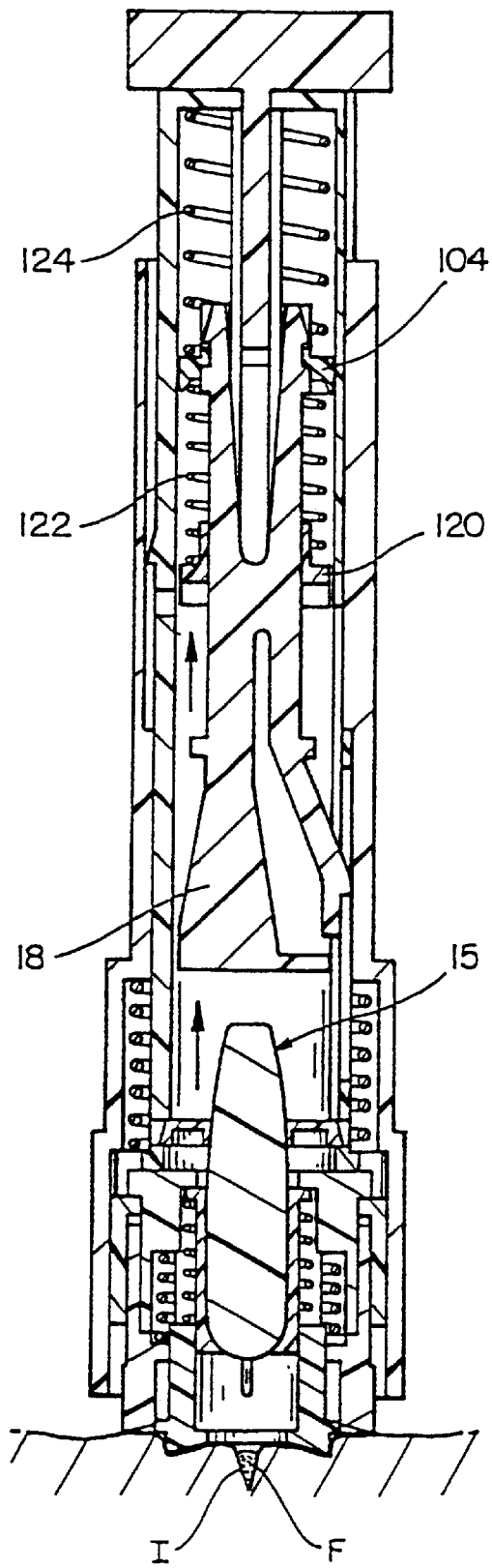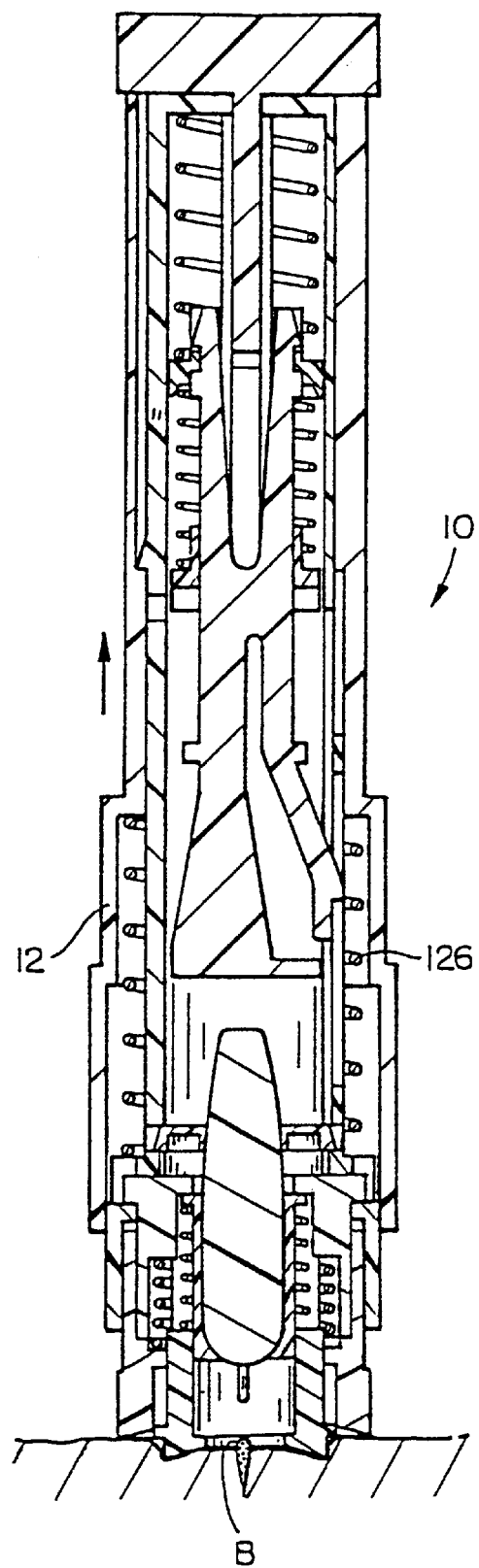
FIG_13H    FIG_13I

BODY FLUID SAMPLING DEVICE

PRIOR APPLICATIONS

The present invention is related to inventions disclosed in the following commonly assigned U.S. applications: Ser. No. 08/858,045; Ser. No. 08/857,335; Ser. No. 08/858,042; Ser. No. 08/858,043; and Ser. No. 08/857,680, all filed on May 16, 1997. The disclosures of those applications are incorporated herein by reference.

FIELD OF THE INVENTION

The present invention relates to lancing devices and methods for obtaining samples of blood and other fluids from the body for analysis or processing.

BACKGROUND OF THE INVENTION

Many medical procedures in use today require a relatively small sample of blood, in the range of 5–50 $\mu L$. It is more cost effective and less traumatic to the patient to obtain such a sample by lancing or piercing the skin at a selected location, such as the finger, to enable the collection of 1 or 2 drops of blood, than by using a phlebotomist to draw a tube of venous blood. With the advent of home use tests such as self monitoring of blood glucose, there is a requirement for a simple procedure which can be performed in any setting by a person needing to test.

Lancets in conventional use generally have a rigid body and a sterile needle which protrudes from one end. The lancet may be used to pierce the skin, thereby enabling the collection of a blood sample from the opening created. The blood is transferred to a test device or collection device. Blood is most commonly taken from the fingertips, where the supply is generally excellent. However, the nerve density in this region causes significant pain in many patients. Sampling of alternate sites, such as earlobes and limbs, is sometimes practiced to access sites which are less sensitive. These sites are also less likely to provide excellent blood samples and make blood transfer directly to test devices difficult.

Repeated lancing in limited surface areas (such as fingertips) results in callous formation. This leads to increased difficulty in drawing blood and increased pain.

To reduce the anxiety of piercing the skin and the associated pain, many spring loaded devices have been developed. The following two patents are representative of the devices which were developed in the 1980's for use with home diagnostic test products.

Cornell et al. U.S. Pat. No. 4,503,856 describes a spring loaded lancet injector. The reusable device interfaces with a disposable lancet. The lancet holder may be latched in a retracted position. When the user contacts a release, a spring causes the lancet to pierce the skin at high speed and then retract. The speed is important to reduce the pain associated with the puncture.

Levin et al. U.S. Pat. No. 4,517,978 describes a blood sampling instrument. This device, which is also spring loaded, uses a standard disposable lancet. The design enables easy and accurate positioning against a fingertip so the impact site can be readily determined. After the lancet pierces the skin, a bounce back spring retracts the lancet to a safe position within the device.

In institutional settings, it is often desirable to collect the sample from the patient and then introduce the sample to a test device in a controlled fashion. Some blood glucose monitoring systems, for example, require that the blood sample be applied to a test device which is in contact with a test instrument. In such situations, bringing the finger of a patient directly to the test device poses some risk of contamination from blood of a previous patient. With such systems, particularly in hospital settings, it is common to lance a patient, collect a sample in a micropipette via capillary action and then deliver the sample from the pipette to the test device.

Haynes U.S. Pat. No. 4,920,977 describes a blood collection assembly with lancet and microcollection tube. This device incorporates a lancet and collection container in a single device. The lancing and collection are two separate activities, but the device is a convenient single disposable unit for situations when sample collection prior to use is desirable. Similar devices are disclosed in Sarrine U.S. Pat. Nos. 4,360,016, and O'Brien 4,924,879.

Jordan et al. U.S. Pat. Nos. 4,850,973 and 4,858,607, disclose a combination device which may be alternatively used as a syringe-type injection device and a lancing device with disposable solid needle lancet, depending on configuration.

Lange et al. U.S. Pat. No. 5,318,584 describes a blood lancet device for withdrawing blood for diagnostic purposes. This invention uses a rotary/sliding transmission system to reduce the pain of lancing. The puncture depth is easily and precisely adjustable by the user.

Suzuki et al. U.S. Pat. Nos. 5,368,047, Dombrowski 4,654,513 and Ishibashi et al. 5,320,607 each describe suction-type blood samplers. These devices develop suction between the lancing site and the end of the device when the lancet holding mechanism withdraws after piercing the skin. A flexible gasket around the end of the device helps seal the end around the puncture site until adequate sample is drawn from the puncture site or the user pulls back on the device.

Garcia et al. U.S. Pat. No. 4,637,403 and Haber et al. 5,217,480, disclose combination lancing and blood collection devices which use a diaphragm to create a vacuum over the wound site.

Erickson et al. U.S. Pat. No. 5,582,184 describes a means of collecting and measuring body fluids. This system uses a coaxial syringe and capillary tube disposed within a spacer member. The spacer member limits the depth of syringe penetration, and compresses body tissue around the syringe while the syringe is in the skin, for improving the flow of interstitial fluid to the incision. However, it will be appreciated that the incision will tend to close against the syringe, thereby limiting any advantage that can be achieved.

Single use devices have also been developed for single use tests, i.e. home cholesterol testing, and for institutional use to eliminate cross-patient contamination multi-patient use. Crossman et al. U.S. Pat. No. 4,869,249, and Swierczek U.S. Pat. No. 5,402,798, also disclose disposable, single use lancing devices.

U.S. Pat. Nos. 5,421,816; 5,445,611; and 5,458,140 disclose, as a replacement for invasive sampling, the use of ultrasound to act as a pump for expressing interstitial fluid directly through intact (non-lanced) skin. The amount of fluid which can be obtained in that way is very limited, however.

The disclosures of the above patents are incorporated herein by reference.

Even with the many improvements which have been made, the pain associated with lancing remains a significant issue for many patients. The need for blood sampling and the fear of the associated pain is also a major obstacle for the millions of diagnosed diabetics, who do not adequately monitor their blood glucose due to the pain involved. Moreover, lancing to obtain a blood sample for other diagnostic applications is becoming more commonplace, and a less painful, minimally invasive device is needed to enhance those applications and make those technologies more acceptable.

An object of the present invention therefore, is to provide a device and a method for obtaining a sample of bodily fluid through the skin which is virtually pain free and minimally invasive.

Furthermore, known lancing devices include manually actuable buttons for triggering the lance-driving mechanism once the user has placed the device against his/her skin. Because the user knows the precise instant when the lancet will be triggered, there is a tendency for the user to jerk or raise the device at the instant of triggering, which can lead to inconsistent skin penetration, or possibly no penetration. Therefore, a further object of the invention is to provide a lancing device which eliminates such a tendency on the part of the user.

Moreover, known carriers for supporting disposable lancets are configured to permit the disposable to be inserted and removed solely through a lower end thereof. That requires that a user grasp a lower portion of the disposable in order to push it upwardly or pull it downwardly. Since the needle projects from a lower end of the disposable, the user's hand will be in the immediate vicinity of the needle, and thus exposed to potential injury and/or contamination. Also, the disposable is typically held in the carrier by friction fit. Due to normal manufacturing tolerances, it is difficult to ensure a sufficiently tight fit for the disposable; there may be a tendency for the disposable to wobble, thereby increasing the amount of pain inflicted during a lancing step.

Therefore, it is another object of the invention to provide a lancet carrier which eliminates the above-mentioned shortcomings.

Another object of this invention is to provide a method which can result in a sample of either blood or interstitial fluid, depending on the sample site and the penetration depth utilized. While there are no commercially available devices utilizing interstitial fluid (ISF) at this time, there are active efforts to establish the correlation of analytes, such as glucose, in ISF compared to whole blood. If ISF could be readily obtained and correlation is established, ISF may be preferable as a sample since there is no interference of red blood cells or hematocrit adjustment required.

Another object of this invention is to provide a method which can draw a small but adjustable sample, i.e. 3 $\mu L$ for one test device and 8 $\mu L$ for another test device, as appropriate.

SUMMARY OF THE INVENTION

The present invention relates to a sampling device for sampling blood or interstitial fluid. The device comprises a manually grippable sleeve defining a longitudinal axis, a carrier adapted to support a skin-lancing medium, such as a lancet or laser for example, for producing an incision in skin, and a ring projecting from a longitudinal forward end of the sleeve and mounted for longitudinal movement relative to the sleeve. The ring includes a front stimulator surface adapted to contact a skin surface. An elastically deformable force-transmitting element is operably disposed between the sleeve and the ring for transmitting a force from the sleeve to the ring in response to forward movement of the sleeve relative to the ring, to press the stimulator surface against the skin surface. The stimulator surface is configured to depress a ring-shaped portion of skin and body tissue disposed in surrounding relationship to a skin incision, causing the incision to bulge and the side of the incision to open, whereby body fluid is forced from the incision. Alternatively, the device may omit the carrier, whereby the lancing would be performed by a separate device.

Preferably, all of the parts of the device are of one piece and assembled together without the aid of separate fasteners.

The ring preferably constitutes an inner ring, with the device further including an outer ring arranged in telescoping relationship around the inner ring. The outer ring projects forwardly from the sleeve and is longitudinally moveable relative to the sleeve. A spring elastically biases the outer ring forwardly. The outer ring is movable longitudinally relative to both the sleeve and the inner ring.

The invention also relates to a device having a stimulator surface inclined relative to a plane oriented perpendicular to the axis. The inclination is radially inward and longitudinally rearward. The inclination relative to the plane is from 10 to 65 degrees. A width of the stimulator surface is preferably from about 5 mm to about 20 mm. An inner diameter of the stimulator surface is preferably no smaller than about 6.0 mm.

BRIEF DESCRIPTION OF THE DRAWING

The objects and advantages of the invention will become apparent from the following detailed description of a preferred embodiment thereof in connection with the accompanying drawing in which like numerals designate like elements and in which:

FIG. 1 is a side elevational view of a sampling device according to the present invention;

FIG. 2 is a longitudinal sectional view through a tip assembly according to the invention, with a disposable mounted therein;

FIG. 3 is a front perspective view of a housing component of the sampling device;

FIG. 4 is a longitudinal sectional view taken through the housing depicted in FIG. 3;

FIGS. 5, 6, and 7 are exploded perspective views of the tip assembly;

FIG. 8 is a rear perspective view of an outer ring component of the tip assembly;

FIG. 9 is an exploded perspective view of a hammer assembly of the sampler according to the invention;

FIG. 10 is an exploded perspective view of the hammer assembly and the housing of FIG. 3;

FIG. 11 is an exploded perspective view of the housing and sleeve components of the sampler;

FIG. 12 is an exploded perspective view of the entire sampler; and

FIGS. 13A–13I are longitudinal sectional views taken through the sampler depicting a sequence of operation thereof.

DETAILED DESCRIPTION OF A PREFERRED EMBODIMENT OF THE INVENTION

A minimally invasive sampling device 10 shown in the figures (e.g., see FIGS. 1 and 13A) includes a tubular sleeve 12 in which a tubular housing 14 is telescopingly disposed. The sleeve 12 and housing 14 define a common longitudinal axis A. The housing 14 includes a open front end adapted to receive a detectable lancet tip assembly 16 (see also FIG. 2) which serves to carry a disposable lancet member 15 (hereinafter a "disposable") and to stimulate a skin puncture site, as will be explained subsequently.

Also mounted in the housing 14 are a hammer 18 for displacing the disposable forwardly in a skin-piercing direction, a manual handle 20 for retracting the hammer rearwardly to a cocked (i.e., forwardly biased) position, and a plurality of springs for achieving proper movement of the above-described parts.

The tip assembly 16 includes an inner ring 22, an outer ring 24, an adapter 26, an outer ring spring 28, a carrier 30, and a carrier spring 32. The inner ring 22 includes a generally hollow cylindrical body having a radially outwardly projecting flange 34 near its front end, and a pair of rearwardly projecting mounting legs 36 at its rear end. Each leg 36 includes a beveled rear surface 38 inclined obliquely relative to the axis A, each surface 38 forming a hook having a forwardly facing shoulder 40. A forwardly facing front surface 42 of the inner ring is inclined obliquely relative to the axis for reasons to be explained in greater detail hereinafter.

The outer ring 24 comprises a hollow generally cylindrical body which includes circumferentially spaced recesses 46 on its outer periphery to enable a user to more easily rotate the tip assembly 16 as will be explained. An inner surface of the outer ring 24 includes axial channels 47 (FIG. 8) for reasons to be discussed. A forwardly facing front surface 48 of the outer ring 24 is oriented obliquely relative to the axis A as will be discussed later. A radially inwardly projecting flange 50 is disposed on the outer ring 24 at a location spaced behind the bottom surface 48.

The inner ring 22 is adapted to fit coaxially inside of the outer ring 24, with the outer ring spring 28 seated on the flange 50.

The carrier 30 is adapted to fit inside of the inner ring 22, with the carrier spring 32 seated on an internal rearwardly facing shoulder 52 of the inner ring. A radially outer flange 54 disposed at a rear end of the carrier 30 rests upon a rear end of the carrier spring.

The inner surface of the carrier 30 is of reduced diameter at its lower end to form a seat 56 upon which the disposable 15 rests after being inserted forwardly through an upper end of the carrier.

The disposable 15 can be of any desirable configuration, but preferably comprises a one-piece plastic body molded around a metal lancet 53. The body is of generally X-shaped cross section formed by four ribs 55 which taper-down in a rearward direction whereby front ends of the ribs 55 rest on the seat 56 of the carrier 30. The body also includes an integrally molded cap 57 (see FIG. 13C) which can be twisted and broken-off to expose the lancet 53 after the disposable has been installed in the tip assembly 16 (FIG. 13D).

The adapter 26 includes a cylindrical split skirt 60 which fits telescopingly within the outer ring. The skirt 60 includes axial ribs 62 which fit into the channels 47 of the outer ring 24 to lock the outer ring and adapter together for common rotation. At its upper end the adapter 26 includes a rearwardly facing, radially inwardly projecting shoulder 64 (see FIG. 13B) which supports the shoulders 40 of the legs 36 of the inner ring 22 when the adapter 26 is snapped onto those legs.

Disposed at a rear end of the adapter is a radially outwardly projecting flange structure which includes a pair of diametrically opposed, forwardly facing shoulders 70 (one shoulder 70 shown in FIG. 7) that are inclined obliquely with respect to the axis A. Preferably, the shoulders 70 extend along a generally helical path. Situated circumferentially between those shoulders 70 are a pair of radially outwardly, rearwardly facing shoulders 72 (one shoulder 72 shown in FIG. 7) which are also inclined obliquely with respect to the axis A, e.g., by extending along a helical path that is axially offset with respect to the path of the shoulders 70. There are thus formed diametrically opposed, axial gaps 74 between the shoulders 70, 72 (one gap 74 shown in FIG. 7), to enable the adapter to be attached to the housing 14, as will be explained.

The housing 14 is of hollow, generally tubular shape and includes a front portion 80 that is of larger diameter than a rear portion 82 thereof (see FIGS. 3 and 4). The rear end of the front portion includes a pair of diametrically opposed locking lugs 84 (see FIG. 4). After the adapter 26 has been inserted into the lower portion 80 of the housing 14 with the lugs 84 situated behind the rearwardly facing shoulders 72 of the adapter (as shown in phantom in FIG. 7), rotation of the adapter in a clockwise direction in FIG. 12 will cause the forwardly facing shoulders 70 of the adapters to engage top surfaces of respective lugs 84 to cause the adapter 26 and housing 14 to converge axially and become locked together, in effect, by a screw-thread type of coupling.

The housing 14 further includes a spring finger 90 having a forwardly facing shoulder 92 (FIG. 4) for engaging a rearwardly facing shoulder 94 located on an inner surface of the sleeve 12 (FIG. 13A) in order to retain the housing 14 within the sleeve 12. In addition, the housing 14 includes a latching lug 96 spaced radially outwardly with respect to a rear section of the rear portion 82 of the housing 14, as can be seen in FIG. 13A. That latching lug 96 is slidable within a longitudinal latch groove 98 formed in an inner surface of the sleeve 12, and is arranged to hold the hammer 18 in a cocked state.

The hammer 18 is slidably mounted within the housing 14 and includes a front abutment surface 100 and a pair of rear mounting arms 102 having hooks configured to become locked by snap fit to a retainer 104 that is slidably mounted in the housing (see FIGS. 9 and 13A). The hammer 18 further includes a latching finger 106 having a forwardly facing shoulder 108 arranged to engage the latching lug 96 of the housing 14 when the hammer is in a cocked state. The latching finger 106 is slidable within the latch groove 98 to prevent rotation of the hammer.

Extending forwardly through a rear opening 110 formed in the rear end of the housing 14 is a tongue 111 of the knob 20. The tongue 111 includes a pair of spring legs 112. Front ends of the spring legs 112 form hooks 114 arranged to engage a front end of a collar 120 that is disposed on the outer periphery of the hammer 18.

A knob spring 122 acts between the retainer 104 and the collar 120, and a hammer spring 124 acts between the rear of the housing 14 and the retainer 104. A sleeve spring 126 acts between a forwardly facing shoulder 128 of the sleeve 12 and a rearwardly facing shoulder 130 of the housing 14.

A keeper member 132 (FIGS. 12, 13A) snaps into a recess 134 of the housing 14. The keeper member 132 includes a rearwardly tapering center hole 136 for preventing a disposable 15 from moving rearwardly (see FIG. 13C) in the event that the sampler 10 is held with the front end directed upwardly.

Assembling The Sampler

To assemble the above-described apparatus, the parts of the tip assembly 16 is first assembled together by inserting the inner ring 22 into the outer ring 24 and placing the outer ring spring 28 onto the spring ring 22. Then, the carrier spring 32 is placed into the inner ring 22 and the carrier 30 adapter 26 is snapped onto the legs 36 of the inner ring.

The main body is assembled by sliding the collar 120 onto the hammer 18, and inserting the knob spring 122 over the hammer. The retainer 104 is then snapped onto the mounting arms 102 of the hammer 18 to capture the knob spring 122 therebetween. The hammer spring 124 is then inserted onto the retainer 104.

The resulting hammer subassembly 105 is then inserted into the housing 14 (see FIG. 10) with the latching finger 106 aligned with the latch groove 98. The sleeve spring 126 and the sleeve 12 are then placed over the housing, and the knob 20 is inserted through the rear opening 110 of the housing so that the spring legs 112 thereof travel through the retainer 104 and the knob spring 122 and become snapped into the collar 120.

The keeper member 132 is inserted into the recess 134 formed in the housing 14, and the tip assembly 16 is installed rearwardly into the housing until the locking lugs 84 of the housing engage the shoulders 72 of the adapter. Then, the tip assembly is rotated (by rotating the outer ring 24) to cause the locking lugs 84 to pass circumferentially through respective ones of the gaps 74 (see FIG. 7). The shoulders 26 of the adapter come to overlie the lugs 84 and secure the tip assembly within the housing.

Using the Sampler

In order to use the apparatus, the tip assembly 16 is removed by rotating the outer ring 24 and adapter 26 counter clockwise in FIG. 7, and a disposable 15 is inserted forwardly through the back of the carrier 30. Then, the tip assembly is reinstalled (FIG. 13C), and the cap 57 of the disposable is manually twisted and broken off (FIG. 13D) to expose the lancet 53.

The knob 20 is then pulled rearwardly to cause the hammer 18 to be pulled rearwardly (FIG. 13D). The latching finger 106 of the hammer travels upwardly past the latching lug 96. As this occurs, the knob spring 122 and hammer spring 124 are compressed. By then releasing the knob 20, the knob spring 122 pulls the knob 20 forwardly, and the hammer spring 124 pushes the hammer forwardly until the shoulder 108 of the latching finger abuts the latching lug 96 (FIG. 13E). The hammer is now in a cocked state.

The front surface 48 of the outer ring 24 is now placed against the user's skin S, and the user, gripping the sleeve 12, pushes the sleeve 12 toward the user's skin S. Consequently, the outer ring 24 travels rearwardly relative to the inner ring 22, causing the outer ring spring 28 to be compressed. This occurs until the front surface 42 of the inner ring 22 engages the skin surface S (FIG. 13F). Further downward force on the sleeve 12 causes the sleeve 12 to travel forwardly relative to the housing 14. As that occurs, the latching finger 106 is engaged and cammed inwardly by a portion 150 of the inner surface of the sleeve 12, whereby the latching finger 106 becomes released from the latching lug 96. This enables the previously-compressed hammer spring 124 to displace the hammer 18 forwardly against the rear end of the disposable 15 (FIG. 13G), whereby the disposable, along with the carrier 30, are displaced forwardly, causing the carrier spring 32 to be compressed. As the disposable 15 travels forwardly, the lancet 53 punctures the skin surface and forms an incision I therein, whereafter the carrier spring 32 immediately retracts the carrier 30 and the disposable 15 (FIG. 13H).

The forward force being applied to the sleeve 12 is transmitted to the inner ring 22 through the compressed sleeve spring 126, the housing 14, and the adapter 26. The front surface 42 of the inner ring 22 thus depresses a ring-shaped portion of the skin and body tissue disposed in surrounding relationship to the incision I, causing the incision to bulge while pulling apart the sides of the incision. Hence, fluid F such as blood or interstitial fluid is trapped by the depressed body tissue and skin and pressurized so that it travels upwardly through the pulled-open end of the bulging incision. That is, the surrounding ring of depressed skin and body tissue restricts the outward flow of fluid away from the incision.

When the forward force on the sleeve 12 is released (FIG. 13I) the sleeve is retracted by the sleeve spring 126, causing the force applied by the inner ring 22 against the skin to be relieved. According, the sides of the incision I close, and fresh fluid (previously blocked by the depressed skin and body tissue) flows toward the incision to replace the fluid which had been forced from the incision. As the forward force is reapplied to the sleeve and thus to the inner ring (see FIG. 13H), the above-described action is repeated, and additional fluid is forced upwardly through the incision. Eventually, this "pumping" action results in the formation of a suitably large drop B of body fluid capable of being sampled.

Although the front face of the inner ring 22 is disclosed as being generally annular, it could be of other configurations such as oval or polygonal, whereby the ring of depressed body tissue would be similarly configured.

Certain optimal dimensional characteristics of the front surface i.e., the stimulator surface 42, of the inner ring 22 have been developed, for maximizing a flow of recoverable body fluid. In that regard, the angle of inclination $\alpha$ of the face 42 relative to a plane P extending perpendicular to the axis A should be from about 10 to about 65 degrees, more preferably 25 to 65 degrees (see FIG. 13F). A width W of the face 42 (i.e., the outer diameter of the inner ring minus the inner diameter thereof) should be from about 5 mm to about 20 mm. The inner diameter of the surface 42 should be no smaller than about 6.0 mm, and no larger than about 12.0 mm. By inclining the stimulator surface 42 within the above stated range of angles $\alpha$, it is assured that a sufficient amount of body fluid displaced by that surface will flow toward the incision. By making the inner diameter no smaller than 6.0 mm, the surface 42 will not tend to contact and smear a blood drop B of suitable sampling size (i.e., 3 microliters).

By applying the forward "pumping" force from the sleeve 12 to the inner sleeve through the medium of an elastic force transmitting member, i.e., the sleeve spring 126, the force is applied for a prolonged dwell period during forward movement of the sleeve 12 relative to the housing 14. This enables more of the blood or interstitial fluid confined around the area of the incision I to be pushed upwardly therefrom.

Except for the needle 53 and the springs 28, 32, 122, 124 and 126, the parts of the sampling device 10 are preferably formed of plastic. All of the plastic parts are of one-piece structure (i.e., gluing of segments together to form a part is avoided). Also, all of the plastic parts are attached together in the absence of separate fasteners, e.g., by snap couplings, or by a screw-thread coupling (i.e., in the case of the attachment of the adapter 26 to the housing 14). This greatly simplifies the construction of the sampler device and reduces its manufacturing cost.

It will be appreciated that the device 10 provides for an automatic triggering of the hammer in response to a pressing of the device against the skin. This eliminates any tendency for the user to jerk the device upwardly at the instant of triggering, because the user is not aware of the triggering instance, and ensures that penetrations of constant depth will be performed from one lancing operation to the next.

The ability to load and unload a disposable into the tip assembly 16 through an upper end thereof means that the user can keep his/her hands remote from the lancet. This ensures against accidental wounding, possibly by a contaminated lancet. The four-point securement of the disposable within the carrier, as defined by the four projections 55 of the disposable, creates a stable movement-free mounting of the disposable within the carrier. Hence, the disposable will not tend to move laterally during a lancing procedure, thereby reducing the amount of pain that may be experienced by the user.

The ability of the device to pump body fluids such as blood or interstitial fluid to the skin surface enables the device to be used to lance the skin at areas of the body which are less susceptible to pain, such as the arm for example.

Although the present invention has been described in connection with a preferred embodiment thereof, it will be appreciated by those skilled in the art that additions, modifications, substitutions and deletions not specifically described may be made without departing from the spirit and scope of the invention as defined in the appended claims.

What is claimed is:

1. A sampling device for sampling blood or interstitial fluid, comprising:
    a manually grippable sleeve defining a longitudinal axis;
    a carrier adapted to support a skin-lancing medium for producing an incision in skin;
    a ring projecting from a longitudinal forward end of the sleeve and mounted for longitudinal movement relative to the sleeve, the ring including a front stimulator surface adapted to contact a skin surface; and
    an elastically deformable force-transmitting element operably disposed between the sleeve and ring for transmitting a force from the sleeve to the ring in response to forward movement of the sleeve relative to the ring, to press the stimulator surface against the skin surface, the stimulator surface configured to depress a ring-shaped portion of skin and body tissue disposed in surrounding relationship to a skin incision, causing the incision to bulge and the sides of the incision to open, whereby body fluid is forced from the incision.

2. The sampling device according to claim 1, wherein the ring constitutes an inner ring, the device further including an outer ring arranged in telescoping relationship around the inner ring, the outer ring projecting forwardly from the sleeve and being longitudinally movable relative to the sleeve; and a spring elastically biasing the outer ring forwardly, the outer ring being movable longitudinally relative to both the sleeve and the inner ring.

3. The sampling device according to claim 2, further including a housing mounted in the sleeve for longitudinal movement relative thereto, a trigger mounted in the housing for longitudinal movement relative thereto, the housing and trigger together defining a latching structure for releasably latching the trigger in a spring-biased cocked state, the latching structure being releasible in response to rearward movement of the housing relative to the sleeve.

4. The sampling device according to claim 3, further including an adapter connected to the ring by a snap-coupling, and connected to the housing by a bayonet coupling.

5. The sampling device according to claim 1 wherein the stimulator surface is inclined relative to a plane oriented perpendicular to the axis, the inclination being radially inwardly and longitudinally rearwardly, the inclination relative to the plane being from 10 to 65 degrees.

6. The sampling device according to claim 5 wherein a width of the stimulator surface is from about 5 mm to about 20 mm.

7. The sampling device according to claim 6 wherein an inner diameter of the stimulator surface is no smaller than about 6.0 mm.

8. The sampling device according to claim 7 wherein the inner diameter is no larger than about 12.0 mm.

9. The sampling device according to claim 1 wherein a width of the stimulator surface is from about 5 mm to about 20 mm.

10. The sampling device according to claim 9 wherein an inner diameter of the stimulator surface is from about 6.0 mm to about 12.0 mm.

11. The sampling device according to claim 1 wherein an inner diameter of the stimulator surface is no smaller than about 6.0 mm.

12. The sampling device according to claim 11 wherein the inner diameter is no larger than about 12.0 mm.

13. The sampling device according to claim 1, further including a housing mounted in the sleeve and being longitudinally movable relative to the sleeve; an adapter attached to the housing and carrying the ring and carrier; a collar disposed in the housing; a retainer disposed in the housing in rearwardly spaced relationship to the collar; a cocking spring operably disposed between the retainer and collar; a hammer having a rear end attached to the retainer; a hammer spring arranged for biasing the hammer forwardly toward the carrier; a manual hammer-cocking knob having a manually grippable rear end projecting from the housing and sleeve, and a front end attached to the collar; the housing forming a stop for releasably latching the hammer in a cocked state.

14. The sampling device according to claim 13 wherein the ring and adapter form a first coupling independent of a separate fastener; the adapter and housing forming a second coupling independent of a separate fastener; the housing and sleeve forming a third coupling independent of a separate fastener; the hammer and retainer forming a fourth coupling independent of a separate fastener; and the cocking knob and collar forming a fifth coupling independent of a separate fastener.

15. The sampling device according to claim 14 wherein each of the first, third, fourth and fifth couplings is a snap-in coupling.

16. The sampling device according to claim 1, in combination with a lancet mounted in the carrier; a keeper mounted in the sleeve behind the carrier for preventing rearward movement of the lancet.

17. A sampling device for sampling blood or interstitial fluid, comprising:
    a manually grippable sleeve defining a longitudinal axis; and
    a ring projecting from a longitudinal forward end of the sleeve and mounted for longitudinal movement relative to the sleeve, the ring including a front stimulator surface adapted to contact a skin surface, wherein the stimulator surface is inclined relative to a plane oriented perpendicular to the axis, the inclination being radially inwardly and longitudinally rearwardly, the inclination relative to the plane being from 10 to 65 degrees, a width of the stimulator surface being from about 5 mm to about 20 mm, an inner diameter of the stimulator surface being no smaller than about 6.0 mm.

18. The sampling device according to claim 17 further including a carrier adapted to support a skin-lancing medium for producing an incision in skin.

19. A sampling device for sampling blood or interstitial fluid, comprising:

a manually grippable sleeve defining a longitudinal axis;

a ring projecting from a longitudinal forward end of the sleeve and mounted for longitudinal movement relative to the sleeve, the ring including a front stimulator surface adapted to contact a skin surface; and an elastically deformable force-transmitting element operably disposed between the sleeve and ring for transmitting a force from the sleeve to the ring in response to forward movement of the sleeve relative to the ring, to press the stimulator surface against the skin surface, the stimulator surface configured to depress a ring-shaped portion of skin and body tissue disposed in surrounding relationship to a skin incision, causing the incision to bulge and the sides of the incision to open, whereby body fluid is forced from the incision.

20. The sampling device according to claim 19 wherein the stimulator surface is inclined relative to a plane oriented perpendicular to the axis, the inclination being radially inwardly and longitudinally rearwardly, the inclination relative to the plane being from 10 to 65 degrees.

21. The sampling device according to claim 19 wherein a width of the stimulator surface is from about 5 mm to about 20 mm.

22. The sampling device according to claim 19 wherein an inner diameter of the stimulator surface is no smaller than about 6.0 mm.

23. The sampling device according to claim 19 wherein the stimulator surface is inclined relative to a plane oriented perpendicular to the axis, the inclination being radially inwardly and longitudinally rearwardly, the inclination relative to the plane being from 10 to 65 degrees, a width of the stimulator surface being from about 5 mm to about 20 mm, an inner diameter of the stimulator surface being no smaller than about 6.0 mm.

* * * * *